United States Patent [19]

Grundman

[11] 3,991,175

[45] Nov. 9, 1976

[54] COMPOSITION AND METHOD FOR DETERMINATION OF PREGNANCY

[75] Inventor: Lea Grundman, Jerusalem, Israel

[73] Assignee: Rafa Laboratories Ltd., Israel

[22] Filed: July 25, 1975

[21] Appl. No.: 599,090

Related U.S. Application Data

[63] Continuation-in-part of Ser. No. 202,004, Nov. 24, 1971, abandoned, which is a continuation-in-part of Ser. No. 125,428, March 17, 1971, abandoned.

[30] Foreign Application Priority Data

July 20, 1970 Israel.................................. 34960

[52] U.S. Cl..................................... 424/12; 424/3; 424/100; 424/105
[51] Int. Cl.² ................. A61K 39/00; G01N 31/00; G01N 33/16
[58] Field of Search .................. 424/8, 12, 100, 105

[56] References Cited

UNITED STATES PATENTS

| 3,309,275 | 3/1967 | Treacy | 424/12 |
| 3,322,634 | 5/1967 | Fulthorpe | 424/12 |
| 3,639,558 | 2/1967 | Csizmas | 424/12 |

OTHER PUBLICATIONS

Cayzer, The Lancet, Sat., May 18, 1974 pp. 947–949.

Kwapinski, Method of Serol. Res, John Wiley & Sons N.Y. 1965 pp. 206–211.

Stavitsky, Int. Arch. Allergy, vol. 13, 1958 pp. 1–13.

Primary Examiner—James O. Thomas, Jr.
Assistant Examiner—A. P. Fagelson
Attorney, Agent, or Firm—Steinberg & Blake

[57] ABSTRACT

Compositions for the determination of whether or not a female animal, and particularly a human female, is pregnant are provided which compositions have prolonged shelf life. The compositions comprise chorionic gonadotropin coupled to animal red blood cells by means of glutaraldehyde as coupling agent therebetween as well as anti-chorionic gonadotropin serum and gelatin which has the effect of greatly increasing the shelf life and accuracy over prolonged periods of time of the composition. The body fluid of the female animal suspected of being pregnant is mixed with the above composition and permitted to stand. Agglutination indicates non-pregnancy whereas failure of agglutination indicates pregnancy. The invention further comprises that the specific use of turkey blood or camel blood as the source of the red blood cells, the use of either turkey blood or camel blood greatly reducing the time required for the testing.

14 Claims, No Drawings

COMPOSITION AND METHOD FOR DETERMINATION OF PREGNANCY

CROSS REFERENCE TO RELATED APPLICATIONS

This application is a continuation-in-part of my co-pending application Ser. No. 202,004, filed Nov. 24, 1971 now abandoned, for "Pregnancy Determining Composition and Method," which in turn is a continuation-in-part of application Ser. No. 125,428, filed Mar. 17, 1971, for "A Method for the Determination of Pregnancy and Serodiagnostic Composition Therefor," now abandoned.

BACKGROUND OF THE INVENTION

Pregnancy testing of various types for human beings and for animals is of considerable interest and many different types of tests are known.

Some of the methods are biological in nature and require the use of a specific animal, for example rabbits, mice, frogs, etc. These biological tests have serious drawbacks, for example in requiring the availability and housing of many animals which meets specific requirements. Tests of this type are consequently rather complicated and expensive, also requiring special laboratory techniques and considerable time for arriving at a result. The time required may be several days.

Improvements in testing for pregnancy have been provided which overcome many of these drawbacks, for example tests which do not require special animals or special laboratory techniques. Attempts have also been made to provide tests which can be performed in a physician's office and which can give the desired result within a relatively short time.

Israel Pat. No. 16245 describes serodiagnostic compositions for the diagnosis of pregnancy comprising chorionic gonadotropin hormone combined with sheep red blood cells by means of bis-diazo-benzidine and chorionic gonadotropin hormone antibody. However, these compositions are unsatisfactory from the standpoint of stability. Attempts to overcome this drawback by the addition of formaline, a stabilizing agent, have not been satisfactory because the storage period of the resulting composition was still too short, particularly if resuspended in liquid, and this is a serious drawback.

Attempts have also been made to reduce the time required for the pregnancy determination tests. However, the time in general was always measured in hours, generally in about two hours, rather than in minutes.

SUMMARY OF THE INVENTION

In general the present invention comprises the use of glutaraldehyde as coupling agent between chorionic gonadotropin hormone and animal red blood cells in a composition including gelatin which acts to greatly increase the shelf life of the composition. This composition is mixed with anti-chorionic gonadotropin serum for the actual carrying out of the test. It has further been found in accordance with the present invention that while the red blood cells of any animal (the term "animal" including birds and reptiles) may be used for the purposes of the present invention, that if specifically turkey blood or camel blood is used, the time required for the agglutination test is tremendously reduced.

It is accordingly a primary object of the present invention to provide for new, stable serodiagnostic compositions for the determination of pregnancy.

It is a further object of the present invention to provide such compositions having prolonged storage life and which can be used for the determination of pregnancy of any female animal, particularly humans.

It is yet a further object of the present invention to provide for a method of determining pregnancy utilizing the compositions of the present invention.

It is still a further object of the present invention to provide serodiagnostic compositions for the determination of pregnancy which give the results much more rapidly than hitherto known compositions.

Other objects and advantages of the present invention will be apparent from a further reading of the specification and of the appended claims.

With the above and other objects in view, the present invention mainly comprises a composition which can be used with anti-chorionic gonadotropin serum and with the body fluid of a female to be tested for determining whether or not the female is pregnant, the composition consisting essentially of chorionic gonadotropin coupled to animal red blood cells by means of glutaraldehyde as coupling agent therebetween, the composition also including gelatin. The gelatin acts to increase the shelf life of the composition, particularly when in solution form, by at least 100 times.

As will be described further below in carrying out the test this composition is mixed with anti-chorionic gonadotropin serum and with the body fluid of the female animal being tested for pregnancy. If the female is pregnant, the chorionic gonadotropin in the body fluid reacts with the anti-chorionic gonadotropin serum so that no agglutination occurs, whereas if the female is not pregnant no such reaction can take place and agglutination occurs. The time required for this test is generally about 2 hours and perhaps somewhat longer.

In accordance with a preferred embodiment of the present invention the red blood cells utilized in the composition of the invention is obtained from either turkey blood or camel blood, in which case the time required for the test determination is between about 15 minutes and 20 minutes.

Although this invention is applicable to pregnancy determination of all types of animals by the use of the chorionic gonadotropin of the same type of animal as the animal being tested, of major commercial importance is the determination of whether or not the human female is pregnant. For this purpose it is necessary to use human chorionic gonadotropin coupled to the animal red blood cells by means of glutaraldehyde. Consequently, throughout the specification reference will be had to the determination of pregnancy of the woman, i.e. the human female, and for this purpose reference will generally be made to the use of human chorionic gonadotropin (hereinafter generally referred to as "HCG").

When the animal red blood cells are coupled to the HCG by the glutaraldehyde the blood cells are generally hereinafter referred to as "sensitized cells." The animal red blood cells may be obtained from any animal including mice, sheep, cattle, and even human beings. However, as indicated above, in accordance with the preferred embodiment of the present invention the red blood cells are obtained from turkeys or camels. The advantage of the use of red blood cells from turkeys or camels is the greatly reduced testing time, i.e. to about 15 – 20 minutes on the average, as compared to an average time of 2 hours when the blood cells are obtained from another source.

As indicated above, the addition of gelatin to the sensitized cells composition of the present invention, that is the animal red blood cells coupled to the chorionic gonadotropin by means of the glutaraldehyde greatly increases the storage time of the composition. This increase in storage time of the composition applies whether the red blood cells are obtained from turkeys or camels as in accordance with the preferred embodiment of the present invention, or whether the red blood cells are obtained from any other animal such as sheep. While the addition of the gelatin is also advantageous in somewhat shortening the time required for determination of the pregnancy test, this reduction in time is too little to be of any real consequence. Important reduction in time for carrying out the test is achieved by the use of turkey blood or camel blood as the source of the red blood cells.

The amount of gelatin which is added to the sensitized cells composition should be such as to provide the effect of increased storage time. This effect can be achieved with amounts as little as 0.01% by weight, while amounts greater than 1% by weight are not necessary because the desired increased storability has already been achieved with lower amounts of gelatin. The preferred amount of gelatin added to the composition of the present invention for the purpose of increasing the shelf life or storability thereof is between about 0.01–1% by weight, preferably about 0.05–0.2% by weight, most preferably about 0.1% by weight.

For storage purposes, the sensitized blood cells are preferably first washed with borate-saline solution after which the gelatin may be added for storage purposes. While the stability of the sensitized blood cells is also increased by treating the same with glutaraldehyde or formaldehyde, after the same had been washed with borate-saline solution, it is the addition of gelatin which is most effective in increasing the storage ability of the composition.

For effecting the determination of pregnancy in accordance with the present invention the sensitized blood cells are mixed with an anti-HCG serum and with a body fluid of the woman suspected of being pregnant. The fluid utilized for this purpose may be blood, serum, urine, etc. Most preferably, freshly filtered urine is used.

If the woman is pregnant, then HCG is present in the body fluid and the anti-HCG serum will react with the free HCG in the body fluid so that no reaction will occur between the sensitized cells and the anti-serum. On the other hand, if the woman is not pregnant, in which case the body fluid does not contain free HCG, then the antiserum will cause agglutination of the serodiagnostic composition, that is the sensitized blood cells. As explained above, in the case of the use of blood cells from most sources, such as sheep, this reaction generally occurs after about 2 hours, whereas if the red blood cells are obtained from turkeys or camels, then the reaction occurs within 15-20 minutes.

It is only necessary to utilize small amounts of the composition of the present invention and of the body fluid in order to carry out the pregnancy determination test. In accordance with an embodiment of the invention the method is performed in solution, preferably a solution buffered at pH 5-8.5. However, it is also possible to carry out the method in other forms, for example with the serodiagnostic composition of the invention pressed into a tablet or impregnated on a paper strip or the like. The stored sensitized blood cell composition of the invention can then in suitable manner be brought into contact with the anti-HCG serum and the body fluid of the woman for the pregnancy determination test. As indicated above, the addition of gelatin to the sensitized blood cell composition, whether the blood cells are obtained from turkeys or camels as in the preferred embodiment of the present invention, or from any other animal, has the effect of greatly increasing the shelf life or storeability of the composition. This has been proved by stability tests as described below.

Stability tests were carried out on eight batches of HCG sensitized red blood cells (blood cells obtained from various sources) stored at 0.4% concentration in saline solution buffered at pH 7, with and without the addition of gelatin. All compositions were identical in each batch except for the presence or absence of gelatin. The results are summarized in Table A below:

TABLE A

| Code No. | STORAGE WEEKS | | | | | | | | 2 Years |
|---|---|---|---|---|---|---|---|---|---|
| | 1 | | 2 | | 3 | | 4 | | |
| of Batch | G | NG | G | NG | G | NG | G | NG | only G |
| A | + | + | + | ± | + | − | + | − | + |
| B | + | ± | + | − | + | − | + | − | + |
| C | + | + | + | − | + | − | + | − | + |
| D | + | + | + | − | + | − | + | − | + |
| E | + | + | + | − | + | − | + | − | + |
| F | + | + | + | − | + | − | + | − | + |
| G | + | + | + | ± | + | − | + | − | + |
| H | + | + | + | + | + | − | + | − | + |

G = Gelatin added to concentration of 0.05 – 0.2%.
NG = No gelatin added
+ = Nice patterns, correct results
− = Incorrect results It is thus clear that the shelf life or storeability of the composition of the present invention is increased by at least 100 times by the addition of the gelatin thereto.

In preparing a sensitized blood cells composition of the chorionic gonadotropin coupled to the animal red blood cells by means of glutaraldehyde as coupling agent therebetween it is apparent that the amounts of the various components of the composition should be chosen so that the HCG is properly connected to the red blood cells. It is not desirable to use a large excess of any of the components of the composition.

Under certain conditions, particularly when both the sensitized cells and the anti-HCG serum are lyophilized, they can be mixed together and stored in this form. However, when stored in the ordinary form, for example in refrigerated solution form or on paper strips or on tablets, then the sensitized cells composition and anti-HCG serum are stored separately. The addition of the gelatin to the sensitized cells composition increases the storeability thereof to such extent that lyophilization is ot necessary in order to obtain sufficient storeability for commercial purposes.

In carrying out the method of the invention any known anti-HCG serum may be utilized provided that it is sufficiently specific for the utilized HCG. However, advantageously the anti-HCG serum is prepared as described herein. As is apparent, the amount of the anti-HCG serum which is utilized in the test is ascertained for each serum. This is described below.

DESCRIPTION OF PREFERRED EMBODIMENTS

The following Examples are given to further illustrate the present invention. The scope of the invention is not, however, meant to be limited to the specific details of the Examples.

EXAMPLE 1

A. Preparation of absorbed rabbit anti-HCG serum a. 5 mg of a HCG preparation having a potency of 2800–3000 U/mg were dissolved in 5 ml of phosphate buffer of pH 7.1. The solution obtained was homogenized with an equal volume of complete Freund's adjuvant.

| The phosphate buffer comprised: | |
|---|---|
| $Na_2HPO_4$ anhydride | 16.06 g |
| $Na H_2PO_4.2H_2O$ | 5.85 g |
| $H_2O$ up to | 1000 ml |

The above potency of the HCT preparation is by no means critical for the success of the immunization procedure.

It is readily understood that any other suitable buffer solution may be utilized as long as it fulfills the requirements. The pH range may be varied between 6.5–8.5.

b. 0.1 ml and 0.5 ml of the above homogenate were injected simultaneously into the foot pad and intramuscularly respectively, into a rabbit weighing 2.5–3.0 kg once a week for three consecutive weeks.

c. One week after the last set of injections the rabbits were bled and the serum was separated by centrifugation and stored in a refrigerator.

d. Non-specific antibodies were absorbed from the serum by mixing equal volumes of the serum and of normal human serum (not containing HCG). The mixture obtained is called "absorbed anti HCG serum."

B. Preparation of anti-HCG serum of high dress of purity a. 3 mg of HCG having the same potency as in Example 1A above were dissolved in a phosphate buffer of pH 7.1 prepared as described above and centrifuged for one hour at 15,000 RPM.

b. The supernatant obtained was added to and mixed with 7.5 ml of absorbed anti-HCG serum which had also been previously centrifuged for one hour at 15,000 RPM. and 3.4 ml of borate saline was added and mixed.

The concentration of HCG and the volume of anti-HCG may vary according to the specific batch of the anti-HCG utilized.

The concentration is determined by preparing a precipitation curve and then selecting the optimum concentration.

The borate saline was prepared as follows:

| i | 0.85% | sodium chloride | |
|---|---|---|---|
| ii | $H_3BO_3$ | 12.37 g | |
| | NaOH | 0.52 g | |
| | NaCl | 8.00 g | |
| | $H_2O$ up to | 1000 ml | |

Each 97 ml of i were admixed with 3 ml of ii.

c. The mixture obtained was incubated for 30 min. at 37° C and then left overnight in the refrigerator.

d. The precipitate which formed was then washed 3 times with the above borate saline and finally suspended in 5 ml of borate saline.

e. 5 ml of the suspension were homogenized with 5.0 ml of complete Freund's adjuvant.

The homogenate obtained contains HCG which has been purified by specially binding it to anti-HCG. This preparation was then used for immunizing rabbits (according to A$b$ and A$c$ above) for obtaining anti-HCG antibodies of high degree of purity.

f. The antiserum was diluted 1:2 in normal human serum (not containing HCG) and diluted with borate saline to a suitable concentration and finally lyophilized.

EXAMPLE 2

Preparation of the serodiagnostic composition a. Method A 1 ml of 2.5% of glutaraldehyde solution in a phosphate buffer of pH 7–7.2 was added under constant stirring to the following mixture:

| 0.15 M – 0.5 M phosphate buffer pH 7–7.2 | 10 ml |
|---|---|
| Packed turkey red blood cells | 0.4 ml |

HCG solution (having the same potency as in Example 1A in a phosphate buffer of pH 7.1 having a concentration of 12 mg/ml 0.5 ml.)

Stirring was continued for one hour. The preparation was then washed three times with borate saline, prepared as described in Example 1B.

Following the washings of the HCG sensitized cells with borate-saline, the erythrocytes were resuspended in phosphate buffer 0.15 M, pH 7.2. The volume of buffer was the same as that used in the conjugation of HCG to the erythrocytes. While the suspension was gently stirred 1 ml solution of the same glutaraldehyde solution utilized above before was added to the suspension.

The suspension was kept under gentle and continuous stirring for 1 hour at room temperature followed by 3 days stirring in the cold room (~ 4° C).

After centrifugation (1500 rpm for 10 minutes) the supernatant was discarded and the cells were washed 4 times with borate saline as described above. After the last washing with borate saline the volume of the packed cells was measured and the cells were washed 4 times with 10 volumes of bi-distilled water each time.

Finally the sensitized erythrocytes were resuspended in 10 volumes of PBS containing 0.1% $NaN_3$ and 0.1% gelatin which was prepared as follows:

| 17.5 ml | $Na_2HPO_4$ | 0.15 M + |
|---|---|---|
| 32.5 ml | $KH_2PO_4$ | 0.15 M + |
| 50 ml | saline | (0.85 % naCl) | were admixed together and 100 mg of $NaN_3$ were dissolved in the above solution.

Two ml of gelatin 5% in saline [5 g gelatin in 100 ml saline were melted and sterilized in an autoclave at 121.6° C (2.0 atmospheres) for 30 minutes] were added to 98 ml of the PBS solution described above.

Next day the suspension of HCG-sensitized cells was centrifuged, the supernatant discarded and the packed cells were re-suspended in the same volume of PBS containing 0.1% NaN₃ and 0.1% gelatin. 10 volumes of the diluent per each volume of packed cells. The obtained suspension represents the stock suspension of sensitized erythrocytes which was kept under refrigeration (2° to 8° C).

In another case, following the washings of the HCG sensitized cells with borate saline the cells were treated as follows:

The erythrocytes were re-suspended in saline (NaCl 0.85%) to obtain a 8% suspension (based on packed cell volume).

While the suspension was under gentle and continuous stirring an equal volume of a neutralized formaldehyde solution 1:12 in saline about 3.3 g per 100 ml solution was added to the suspension. The mixture was kept under gentle stirring for 3 days in the cold room (~ 4° C).

The neutralized formaldehyde solution was prepared as follows:

The commercial formaldehyde solution of about 36–37 g per 100 g (about 40 g per 100 ml solution) was first neutralized with 1 M NaOH (glass electrode) and the neutralized formaldehyde solution was diluted with saline 1:12 (1 ml neutralized formaldehyde solution + ml saline).

After centrifugation (1500 rpm for 10 minutes) the supernatant was discarded and the cells were washed 4 times with 10 volumes of bi-distilled water each time.

The cells were re-suspended in 10 volumes of PBS containing 0.1% NaN₃ and 0.1% gelatin, prepared as described above.

The following day the suspension of HCG sensitized cells was centrifuged, the supernatant discarded and the packed cells were re-suspended in the same volume of PBS containing 0.1% NaN₃ and 0.1% gelatin (10 volumes of the diluent to 1 volume of packed cells).

The method may be varied to a large extent. Thus the pH of the phosphate buffer can vary between 5–8.5; the HCG solution can have a concentration of 4–12 mg/ml and the glutaraldehyde a concentration of 1–5%.

The working suspension to be used in the test was prepared before distribution to the customer as follows:

To 1 ml of the stock suspension, 25 ml of PBS containing 0.1% NaN₃ and 0.1% gelatin were added. The working suspension thus obtained was distributed in penicillin Wals for 10 or 20 tests (0.2 ml per test) with an excess of 20% (2.4 ml for 10 tests and 4.8 ml for 20 tests).

Alternatively to 1 ml of the stock suspension, 25 ml of borate saline containing 0.1% NaN₃ and 0.1% gelatin may be added.

b. Method B 1 ml of 2.5% glutaraldehyde solution in phosphate buffer pH 7.1 were added under constant stirring to the following mixture:

| | |
|---|---|
| Borate Buffer pH 8 (see ii, Example 2) | 10 ml |
| Packed Turkey Red Blood Cells | 0.4 ml |
| HCG (potency as in Example 1A) solution in phosphate buffer pH 7.1 12 mg/ml | 0.5 ml |

Stirring continued for one hour. The preparation was washed 3 times with borate saline prepared as described in Example 1B and then stored in a refrigerator.

EXAMPLE 3

Example 2, both method A and method B were repeated, however using camel red blood cells rather than turkey red blood cells. In all other respects the preparation is identical.

With both the serodiagnostic composition of Example 2 and the serodiagnostic composition of this example pregnancy tests as described below were carried out with results obtained within 15 to 20 minutes.

EXAMPLE 4

Standardization of anti-HCG serum

Two fold dilutions in (borate saline) of anti-HCG serum were prepared in suitable test tubes. The volume of the serum in each tube was 0.1 ml. and 0.25 ml of HCG coated red cells prepared as described in Example 2 were added to each test tube. The concentration of the red cells was approx. 0.4% of packed cells. The tubes were shaken and left to stand at room temperature for about 3 hours. At the end point the results were read and the concentration of the highest dilution of the serum which still agglutinated the red cells was determined. This concentration is the end point of the titration and is defined as "one hemagglutination unit."

For routine pregnancy tests a suitable concentration of serum is used which may vary from 2–16 hemagglutination units the optimum being usually 4 hemagglutination units (a serum 4 times more concentrated than the end point).

EXAMPLE 5

Performance of the pregnancy test (Method I)

The following reagents were mixed in a test tube or any other suitable container:

0.1 ml of anti-HCG serum of suitable concentration which was determined as described in Example 4;

0.1 ml of filtered urine of the woman the pregnancy of whom is to be determined; and 0.25 ml of sensitized turkey red blood cells, the concentration of the packed cells being about 0.4%.

The mixture was shaken and left to stand for about 15–20 minutes. If HCG is present in the urine, i.e. the woman is pregnant, it combines with the anti-HCG and therefore no agglutination occurs. If the woman is not pregnant so that there is no HCG in the urine, the anti-HCG is free to agglutinate the turkey red blood cells, as shown by controls to which 0.1 ml borate saline has been added instead of the filtered urine, and this agglutination indicates non pregnancy.

As indicated above, the test is completed within 15–20 minutes. In the case of the use of sheep red blood cells instead of turkey red blood cells in otherwise the same composition as described above, the time required for the test is about 1 hour. In the case of the use of sheep red blood cells and a composition without gelatin, in addition to the decreased storage life of such composition, as described above, the further disadvantage is that the time required for the test is about 3 hours.

In the case of the use of the camel red blood cell composition of Example 3, in the place of the turkey red blood cell composition of Example 2, the time required for the test is about 15–20 minutes, i.e. the same as with turkey red blood cells.

EXAMPLE 6

Performance of the pregnancy test (Method II)

The anti-HCG serum was lyophilized in vials each containing antiserum sufficient for 25 tests. The powder was dissolved by adding to the contents of one vial 5.0 ml of the sensitized turkey red blood cells the concentration being 0.4% of the packed cells.

The reagent was subdivided in amounts of 0.2 ml into test tubes or other suitable containers. To each test tube or container 0.1 ml of filtered urine was added.

The mixtures were shaken and the results were read as in Example 5.

The results of clinical tests performed with preparations manufactured according to the above method are given in the following tables:

TABLE I

CLINICAL RESULTS OBTAINED WITH THE PREPARATION OF EXAMPLE 5;
conc. of serum 2–4–8 hemagglutination units (HU)
0.25 cc 0.4% red blood cells coated with HCG 12 mg/ml
as compared to results obtained with a commercial preparation (CM)

| Ser. No. | 8HU | 4HU | 2HU | CM |
|---|---|---|---|---|
| 1 | − | − | − | − |
| 2 | − | − | − | − |
| 3 | + | + | + | + |
| 4 | + | + | + | + |
| 5 | + | + | + | + |
| 6 | − | − | − | − |
| 7 | + | + | + | + |
| 8 | − | − | − | − |
| 9 | + | + | + | + |
| 10 | − | − | − | − |
| 11 | − | − | − | − |
| 12 | + | + | + | + |
| 13 | − | − | − | − |
| 14 | − | − | − | − |

+ = pregnant
− = non-pregnant

TABLE II

CLINICAL RESULTS OBTAINED WITH THE PREPARATION OF EXAMPLE 4
(conc. of serum 4HU)
0.25 cc 0.4% sheep red blood cells sensitized with HCG 4 mg/ml
as compared to results obtained with a commercial preparation (CM).

| Ser. No. | 4HU | CM |
|---|---|---|
| 1 | − | − |
| 2 | − | − |
| 3 | − | − |
| 4 | − | − |
| 5 | + | + |
| 6 | − | − |
| 7 | + | + |
| 8 | + | + |
| 9 | − | − |
| 10 | − | − |
| 11 | + | + |

+ = pregnant
− = non pregnant

TABLE III

CLINICAL RESULTS OBTAINED WITH THE PREPARATION OF EXAMPLE 3;
(4 HU units) as compared with a commercial preparation
(CM) and with the Quick Hyperhaemia test (QHT)

| 4 HU | CM | QHT |
|---|---|---|
| − | − | |
| − | − | |
| + | + | |
| + | + | |
| + | + | |
| + | + | |
| − | − | |
| − | − | |
| − | − | |
| − | − | |
| + | + | |
| − | − | |
| + | + | |
| − | − | |
| − | − | |
| + | ? | + |
| − | − | |
| + | + | |

TABLE III-continued

CLINICAL RESULTS OBTAINED WITH THE PREPARATION OF EXAMPLE 3;
(4 HU units) as compared with a commercial preparation
(CM) and with the Quick Hyperhaemia test (QHT)

| 4 HU | CM | QHT |
|------|-----|-----|
| −    | −   |     |
| +    | +   |     |
| +    | +   |     |
| −    | −   |     |
| +    | +   |     |

While the invention has been described in particular with respect to specific compositions and testing methods, it is to be understood that variations and modifications of the invention can be made without departing from the spirit or scope thereof.

What is claimed is:

1. Composition for determining whether or not a female animal is pregnant, said composition consisting essentially of chorionic gonadotropin of the same type animal as said female, coupled to animal red blood cells by means of glutaraldehyde as coupling agent therebetween and also including gelatin in an amount sufficient to stabilize said composition.

2. The composition of claim 1 wherein the amount of gelatin is between about 0.01–1% by weight.

3. The composition of claim 1 wherein the amount of gelatin is between about 0.05–0.2% by weight.

4. The composition of claim 1 wherein said female is human and wherein said chorionic gonadotropin is human chorionic gonadotropin.

5. The composition of claim 1 wherein said animal red blood cells are selected from the group consisting of turkey red blood cells and camel red blood cells.

6. The composition of claim 1 wherein said composition is suspended in a solution buffered at a pH of between about 5–8.5.

7. The composition of claim 6 wherein said solution is a saline solution containing boric acid.

8. A composition ready for mixing with a body fluid of a female animal for determination of whether or not said female animal is pregnant, said composition consisting essentially of the composition of claim 1 and including anti-chorionic gonadotropin serum.

9. The composition of claim 8 wherein said female animal is human and wherein said chorionic gonadotropin is human chorionic gonadotropin and wherein said anti-chorionic gonadotropin serum is anti-human chorionic gonadotropin serum.

10. Composition for determining whether or not a female animal is pregnant, said composition consisting essentially of chorionic gonadotropin of the same type animal as said female coupled to red blood cells of an animal selected from the group consisting of turkeys and camels by means of glutaraldehyde as coupling agent therebetween and having been stabilized by further treating the chorionic gonadotropin coupled red blood cells with a stabilizing effective amount of formaldehyde.

11. The composition of claim 10 wherein said female is human and wherein said chorionic gonadotropin is human chorionic gonadotropin.

12. The composition of claim 1 wherein said animal red blood cells are sheep red blood cells.

13. The composition of claim 10 and also including gelatin in an amount sufficient to stabilize said composition.

14. Method for determining whether or not a female animal is pregnant, which comprises mixing the composition of claim 5 with anti-chorionic gonadotropin and with a body fluid of said female animal and permitting said mixture to stand for 15–20 minutes, whereby if the female is not pregnant then agglutination of the animal red blood cells occurs during said standing, whereas if the female is pregnant no such agglutination occurs.

* * * * *